United States Patent [19]

Slilaty et al.

[11] Patent Number: 5,071,743

[45] Date of Patent: Dec. 10, 1991

[54] PROCESS FOR CONDUCTING SITE-DIRECTED MUTAGENESIS

[75] Inventors: Steve N. Slilaty, Ville St-Laurent; Shi-hsiang Shen, Beaconsfield; Susan Lebel, Ville St-Laurent, all of Canada

[73] Assignee: Her Majesty the Queen in right of Canada, as represented by the National Research Council of Canada, Ottawa, Canada

[21] Appl. No.: 427,703

[22] Filed: Oct. 27, 1989

[51] Int. Cl.$^5$ ................... C12Q 1/68; C07H 15/12; C12N 15/00

[52] U.S. Cl. ............................. 435/6; 536/27; 935/77; 935/78

[58] Field of Search ............... 435/6; 536/27; 935/77, 935/78

[56] References Cited

U.S. PATENT DOCUMENTS 4,851,331  7/1989  Vary et al. ................... 435/6
4,885,248  12/1989  Ahlquist ...................... 435/172.3

OTHER PUBLICATIONS

Cress et al., Gene, 49 (186) pp. 9-22.
Dente et al., Nucleic Acids Research, vol. 11, No. 6, (1983) pp. 1645-1655.

Primary Examiner—Robert A. Wax
Assistant Examiner—Mindy B. Fleisher
Attorney, Agent, or Firm—Larson and Taylor

[57] ABSTRACT

The present invention relates to an approach for conducting site-directed mutagenesis using double-stranded DNA templates. The approach involves the development of a method for generating structures capable of directing full-length complementary-strand synthesis from double-stranded plasmid DNA. These structures are formed following heat denaturation and cooling of linearized plasmid DNA molecules in the presence of what is referred to as a "closing oligonucleotide". A "closing oligonucleotide" is a single-stranded oligonucleotide consisting of a sequence complementary to either or both free ends of one of the two plasmid DNA strands. The "closing oligonucleotide" therefore functions as an agent for recircularization of a DNA strand and generation of a primer-circular template structure suitable for polymerase-dependent full-length complementary-strand synthesis and ligation into a covalently-closed heteroduplex DNA molecule. When combined with a mutagenic oligonucleotide and uracil-substituted DNA templates, this approach allows site-directed mutagenesis to be performed directly on double-stranded DNA with a mutant formation efficiency of about 50%, a level amenable to rapid screening by DNA sequencing.

11 Claims, 2 Drawing Sheets

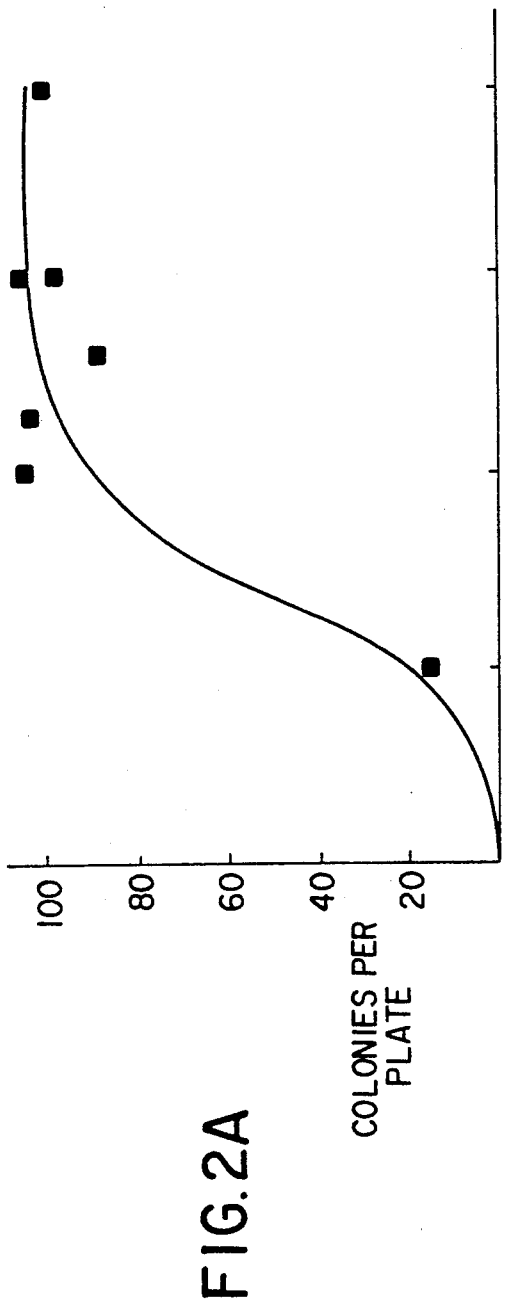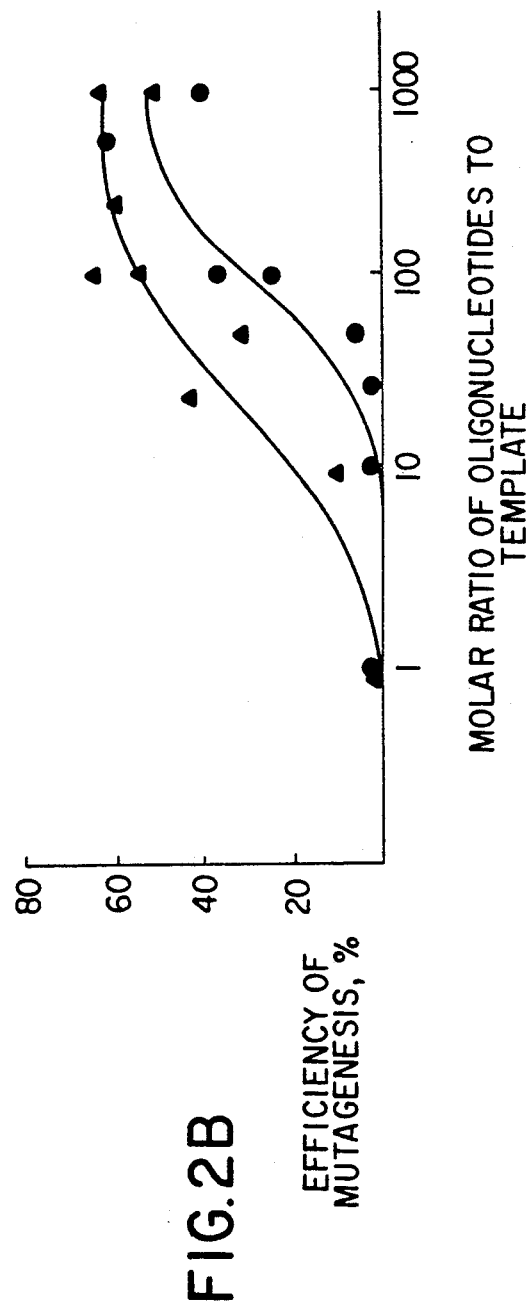
FIG.2A
FIG.2B

PROCESS FOR CONDUCTING SITE-DIRECTED MUTAGENESIS

FIELD OF THE INVENTION

The invention relates to a process for conducting site-directed mutagenesis directly on double-stranded DNA using closing oligonucleotides capable of directing full-length complementary-strand synthesis for linearized double-stranded DNA.

BACKGROUND OF THE INVENTION

Because of its broad applicability, oligonucleotide-directed site-specific mutagenesis embodies a tool fundamental to modern molecular biology research. Its utilization for the introduction of insertions, deletions, and substitutions into coding or non-coding DNA permits the execution of a wide variety of investigations including analysis of structure-function relationships at the level of DNA, RNA, and protein. In the area of enzyme catalysis for example, structural and mechanistic information derived from amino acid substitutions by site-directed mutagenesis continues to add significantly to a wealth of knowledge obtained from biochemical and biophysical studies.

Following the initial reports demonstrating the use of synthetic oligonucleotides to create phenotypically selectable site-specific mutations within φX174 DNA, general methods for site-directed mutagenesis were put forth. Since these developments around ten years ago, many different approaches designed to reduce the time and effort necessary to construct a desired site-specific mutation have been described. In general, these methods fall into two categories: those designed to eliminate the laborious differential hybridization manipulations necessary for identification of the mutant molecules against a large background of parental forms, and the others, aimed at circumventing the requirement for cloning of the target DNA into specialized vectors for the production of single-stranded DNA templates.

An approach which maintains general applicability and high efficiency, and allows site-directed mutagenesis to be performed directly on any existing plasmid would therefore be desirable.

SUMMARY OF THE INVENTION

The present invention provides a novel approach for conducting site-directed mutagenesis directly on double-stranded DNA previously cleaved and denatured to single-stranded linear DNA templates using a closing oligonucleotide.

The process first comprises hybridizing mutagenic and closing oligonucleotides to single-stranded linear DNA templates. The closing oligonucleotide is characterized by having at least part of its nucleotide sequence complementary to at least one of the free ends of said linear DNA templates to direct full-length complementary-strand synthesis and circularization of the linear DNA templates.

Once the hybridizations have been completed, the mutagenic and closing oligonucleotides are incorporated into DNA strands complementary to the linear DNA templates and ultimately into covalently closed DNA circles by submitting the hybridized linear DNA templates to the action of polymerase and ligase enzymes to yield heteroduplex double-stranded DNA molecules.

Finally, the process of the present invention comprises a further step through which selective replication of the synthesized complementary strand of the heteroduplex DNA is performed. It is preferred to use uracil-substituted DNA templates obtained through propagation of the target DNA sequence in a dut$^-$ung$^-$ strain of E. coli as a suitable selection system.

Optionally, the process of the present invention may itself comprise an initial step through which double-stranded DNA is cleaved and denatured to linear single-stranded DNA templates.

Preferably, the closing oligonucleotide referred to above will have at least two different portions of its nucleotide sequence complementary to each free end of the linear DNA template in order to anneal to both free ends thereof, thereby causing circularization of the DNA template. Alternatively, the closing oligonucleotide may have a sequence complementary only to the 3' end of the DNA template.

The process of the present invention may be extended to other types of investigations in which a genetically altered complementary-strand to a prokaryotic or eucaryotic autonomous plasmid or replicon is required.

Also within the scope of the present invention is a kit for conducting site-directed mutagenesis of double-stranded DNA previously cleaved and denatured to single-stranded linear DNA templates. The templates are hybridized to mutagenic and closing oligonucleotides which are in turn incorporated into DNA strands complementary to the template. The kit comprises one or more closing oligonucleotides having at least part of their nucleotide sequence complementary to at least one of the free ends of the single-stranded linear DNA templates, and means for selective replication of the complementary DNA strand. Preferably a dut$^-$ ung$^-$ strain of E. coli such as that referred to above, will be used as a selection means. The kit of the present invention may also contain the appropriate control DNA's and optionally, suitable reagents and buffers.

Finally, the present invention relates to a closing oligonucleotide to anneal to the free ends of a single-stranded linear DNA template whereby circularization of the single-stranded linear DNA template is obtained, the closing oligonucleotide being characterized by having between 10 and 50 nucleotides in length and by having a nucleotide sequence at least complementary to the free ends of the linear DNA template.

Preferably, the closing oligonucleotide is selected from the group consisting of the following:

(AatII) 5'TGGTTTCTTAGACGTCAGGTGCACTTTTC;

(AflIII) 5'CTGGCCTTTTGCTCACATGTTCTTTCCTGC;

(AseI) 5'CTTCCCGGCAACAATTAATAGACTGGATGG;

(MstI) 5'TGGCAACAACGTTGCGCAAACTATTAACTG;

(NdeI) 5'GTATTTCACACCGCATATGGTGCACTCTCA;

(PstI) 5'ACCACGATGCCTGCAGCAATGGCAACAACG;

(PvuI) 5'ACTTCTGACAACGATCGGAGGACCGAAGGA;

(ScaI) 5'ATGACTTGGTTGAGTACTCACCAGTCACAG;

(SspI) 5'AAATGCTTCAATAATATTGAAAAAG-
GAAGA;
(XmnI) 5'TCGCCCCGAAGAACGTTTTCCAAT-
GATGAG; 5'CTGTGACTGGTGAGTACT-
CAACCAAGTCAT;

and complementary sequences thereof.

The present invention will be more readily illustrated by referring to the following description.

IN THE DRAWINGS

FIG. 2 represents the effects of increasing oligonucleotide concentrations on the efficiency of the standard complementary-strand synthesis/site-directed mutagenesis reaction of the present invention.

DETAILED DESCRIPTION OF THE INVENTION

Figure 1:
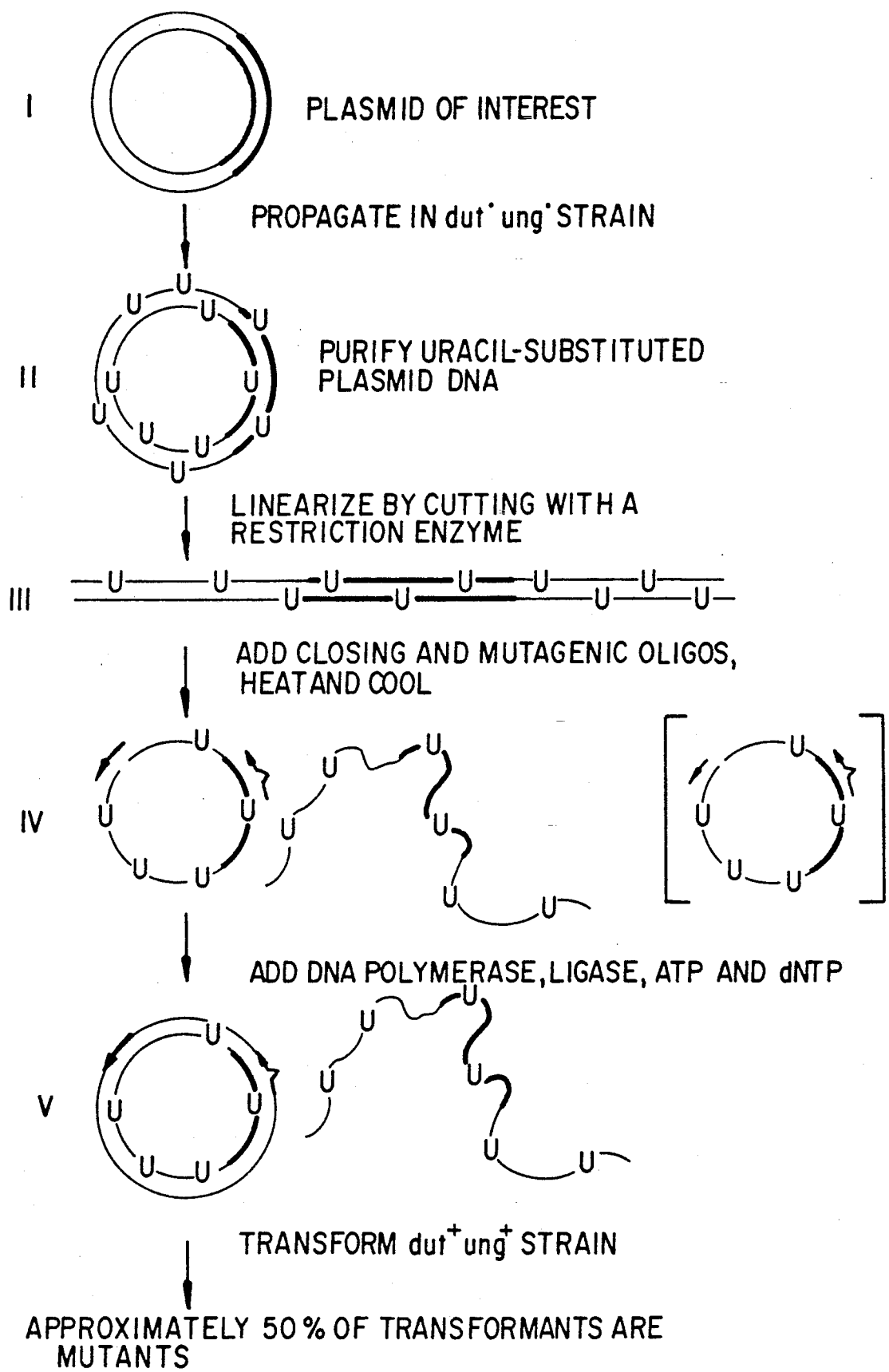
FIG. 1 is a schematic representation of a preferred embodiment of the sequence of steps and expected structures obtained when performing the site-directed mutagenesis reaction of the present invention.

The present invention relates to a novel approach to site-directed mutagenesis of double-stranded DNA. This approach involves the generation of structures capable of directing full-length complementary-strand synthesis of DNA. The structures are formed following heat denaturation and cooling of linear DNA templates in the presence of what will be referred to in the disclosure as a "closing" oligonucleotide. This closing oligonucleotide is a nucleotide sequence having at least part of its sequence complementary to at least one of the free ends of the DNA template. The closing oligonucleotide functions as an agent for circularization of a DNA strand and generation of a primer-circular template structure suitable for polymerase-dependent full-length complementary-strand synthesis and ligation into a covalently-closed heteroduplex DNA molecule.

To develop this new process, it was hypothesized that the time-dependent concentration of single-stranded DNA, available following denaturation of a homogeneous population of linear double-stranded molecules, may be sufficient for use as templates in polymerase-dependent DNA synthesis reactions. Further, it was considered that, during the course of DNA synthesis, the helicase activity of polymerases (E. coli polymerase I, for example) may prove useful for augmenting the level of complementary-strand synthesis by effecting strand displacement in partially reannealed molecules.

Application of the foregoing conditions to actual site-directed mutagenesis experiments requires two additional elements: (i) a closing oligonucleotide, other than the mutagenic one, for directing full-length complementary-strand synthesis and circularization of the linear DNA templates, and (ii) a mechanism for selective replication of the newly synthesized strand in order to obtain high efficiency of mutagenesis.

CLOSING OLIGONUCLEOTIDES

The use of what has been termed a "closing" oligonucleotide meets the requirements for a primer invariably necessary for handling the problem of making full-length copies of linear DNA templates and providing for the resultant double-stranded molecules to be converted into covalently-closed circles by the action of DNA ligase.

Conceptually, two forms of a closing oligonucleotide are possible: an "overlapping" form, which spans the site of linearization by annealing to the free ends of the template strand thereby causing circularization of the DNA strand; or alternatively, a "flush" form which would produce blunt-ended molecules by hybridizing directly to the 3' end of the target template strand. In both cases, the closing oligonucleotide may contain between 10 and 50 nucleotides.

The dependence of this new approach on the use of a closing oligonucleotide and the availability of a unique restriction enzyme site can be met in a general way by designing the closing oligonucleotide to hybridize at any restriction enzyme site with a sequence common to most DNA sequences, such as the plasmid pBR322-derived β-lactamase gene and colE1 replication origin. For example, a closing oligonucleotide may be constructed to span the PstI, PvuI or ScaI sites in the β-lactamase gene or the AflIII or NdeI sites near the origin of replication. In the event any of these sites occur more than once in a particular DNA sequence of interest, linearization may be performed by partial digestion without risk of adversely affecting the reaction since uncleaved, incorrectly cleaved and extensively cleaved molecules have little or no transformation capacity under the present conditions.

The type of oligonucleotide design referred to above would therefore enable the preparation of a single closing oligonucleotide to be employed as a common reagent for a large variety of mutagenesis experiments.

SELECTION SYSTEM

For a selection system, the use of parental DNA which has been uracil-substituted provides a simple and convenient biological approach for preferential survival of the newly synthesized complementary DNA strand and therefore high efficiency mutagenesis.

Uracil-substituted DNA is prepared by propagating the desired DNA template in an E. coli dut⁻ ung⁻ strain. dut⁻ ung⁻ strains are deficient in the enzyme dUTPase, the product of the dut gene, resulting in an increased intracellular pool of dUTP which competes with TTP for incorporation into DNA. Also, uracil incorporated into the DNA strand is not removed because of the deficiency of the dut⁻ ung⁻ strain in producing uracil glycosylase, the enzyme responsible for cleavage of the uracil nucleotides and coded for by the ung gene.

Thus, uracil-substituted DNA is biologically active in a ung⁻ strain incapable of removing uracil. However, the biological activity of uracil-substituted DNA templates is substantially decreased when this DNA is introduced in a ung⁺ host, which will deactivate the template through the action of uracil glycosylase.

As previously shown by Kunkel in *Proc. Natl. Acad. Sci. USA* 82, 488–492 (1985), propagation of a single-stranded target DNA in a dut⁻ ung⁻ strain of E. coli yields uracil-containing templates whose efficiency in transforming dut⁺ ung⁺ strains is 3 to 4 orders of magnitude lower than that of normal DNA. However, in vitro synthesis of a mutagenic strand complementary to the uracil-substituted template through a mutagenic oligonucleotide will lead to a complementary strand free of uracil. This uracil-free complementary strand is still biologically active in a dut⁺ ung⁺ strain of E. coli, even after having been treated with uracil glycosylase prior to transfection, whereas the uracil-containing templates will have been deactivated by such a treatment. Using this method in the context of the present invention, a significant level of transformation efficiency is obtained and 40 to 60% of the transformants have the mutant phenotype.

In fact, the combined use of a closing oligonucleotide to hybridize to a single-stranded DNA template generated from linearized and denatured DNA, and the dut⁻ ung⁻ strain of *E. coli*, provides a process which allows site-directed mutagenesis to be performed directly on double-stranded DNA with a mutant formation efficiency of approximately 50%, a level amenable to rapid screening by DNA sequencing.

However, those skilled in the art will readily appreciate that other selection systems such as incorporation of thionucleotides described by Taylor et al., in *Nucl. Acids Res.* 13, 8749–8785, (1985) or differential methylation may potentially be used in the context of the present invention.

Site-directed mutagenesis using the process of the present invention with a dut⁻ ung⁻ strain of *E. coli* as a selection system.

In order to perform the desired mutagenic reaction on a target DNA strand, the strand in question is first propagated in a dut⁻ ung⁻ strain of *E. coli* and isolated using any suitable technique known to those skilled in the art. Once the desired DNA sequence has been isolated and purified, it is linearized by being reacted with a suitable restriction enzyme if it is in circular form, and subsequently brought to single-stranded form by heat denaturation.

The template DNA thus obtained, will be mixed with the desired closing and mutagenic oligonucleotides. A suitable annealing buffer is added and the reaction mixture may be incubated at a temperature ranging from 70° to 100° C. for a time period ranging from 0.5 to 5 minutes, then optionally cooled at a temperature ranging from 0° to 42° C. for a period ranging from 1 to 15 minutes.

After cooling, a suitable DNA synthesis buffer, DNA ligase and a polymerase are added and the mixture may be incubated at a temperature ranging from 0° to 42° C. for a period ranging from 1 to 5 hours.

The mixture, which contains complete mutagenic DNA strands hybridized to their complementary uracil-substituted DNA templates is then stored at a temperature ranging from 0° to 10° C. or used directly to transform the desired dut+ ung+ cells. The preparation of competent cells and transformation reactions will be performed according to procedures well known in the art, although the method of Hanahan described in *J. Mol. Biol.* 166, 557–580 (1983) is preferred. Following the transformation, the cells harboring the mutagenic DNA strands are selected.

The present invention will be more readily illustrated by referring to the following example.

EXAMPLE 1

Mutagenesis on color indicator systems based on the α-complementation of β-galactosidase.

In order to test the approach of the present invention and to quantitatively evaluate its potential for complementary-strand synthesis and concomitant site-directed mutagenesis, two color indicator systems based on the α-complementation activity of β-galactosidase (lacZβ) were developed.

The system referred to as B2W (blue-to-white) employs a mutagenic oligonucleotide to convert the blue chromogenic plasmid pUC19 described in *Gene* 33, 103–119 (1985) into a colorless plasmid by altering 2 bases to generate a TAA termination codon 29 amino acids downstream from the start of lacZα translation. Simultaneously, a DraI site is created for verification of the presence of the intended changes.

In the second system, referred to as W2B (white-to-blue), the mutagenic oligonucleotide inserts 2 bases into plasmid pSNS282, a colorless derivative of plasmid pUC19. Plasmid pSNS282 was constructed by cleavage of pUC19 DNA with HindIII followed by treatment with Klenow polymerase to fill in the staggered ends and T4 DNA ligase to recircularize the molecules. Following transformation into JM110 as described in *Gene* 33, 103–119 (1985), colorless colonies on plates containing 30 uM isopropyl thiogalactoside (IPTG) and 30 μg/ml 5-bromo-4-chloro-3-indolyl-β-D-galactoside (X-Gal) were analyzed for the presence of a newly created NheI recognition sequence, a subset of which is the in-frame amber triplet ( . . . A AGC TAG CTT . . . ). The 2-base insertion into pSNS282 created by the mutagenic oligonucleotide eliminates the amber codon and leads to a reading frame yielding production of blue colonies. Simultaneous generation of a restriction enzyme site, XhoI, was also included in the system design.

Generation of Linear DNA Templates

Both plasmids were first propagated in the dut⁻ ung⁻ RZ1032 (ATCC #39737) strain described by Kunkel in *Proc. Natl. Acad. Sci., USA* 82, 488–492 (1985), to yield uracil-substituted plasmid DNA. The cultures harbouring either pUC19 or pSNS282 were grown overnight in a medium containing 1.6% Bacto-tryptone, 1% Yeast Extract, 0.5% NaCl and 100 μg/ml ampicillin. The resulting uracil-substituted plasmids were then purified by equilibrium centrifugation in CsCl-ethidium bromide step-gradients as described in *Biochem. Biophys. Res. Commun.* 117, 835–842 (1983). Linearized uracil-substituted templates were prepared by cleavage of the DNA with ScaI followed by extraction with phenol, precipitation with ethanol and resuspension at 50 ng/μl in 1 mM Tris-HCl, pH 8.0, and 0.1 mM EDTA.

PREPARATION OF THE CLOSING AND MUTAGENIC OLIGONUCLEOTIDES

The two closing oligonucleotides, 5'CTGTGACTGGTGAGTACTCAACCAAGT-CAT (overlapping) and 5'ACTCAACCAAGT-CATTCTGAG (flush); and the two mutagenic oligonucleotides, 5'CCCAGTCACGACGTTTTTAAAC-GACGGCCAGTG (B2W, mismatched bases underlined, DraI site in bold) and 5'GCAGGCATG-CAAGCTCGAGCTTGGCGTAATCA (W2B, insertion bases underlined, XhoI, site in bold) were synthesized by the phosphoramidite method using an Applied Biosystems Model 380B DNA synthesizer. Purification of oligonucleotides was performed by precipitation from 2.5M ammonium acetate-83% ethanol followed by washing with 95% ethanol at room temperature.

Purified oligonucleotides were phosphorylated as described in Maniatis et al., *Molecular Cloning, Laboratory Manual*, Cold Spring Harbor Laboratory, Cold Spring Harbor, N.Y. Both the B2W and W2B systems utilize the same closing oligonucleotides which were designed for interaction at the unique ScaI site in the β-lactamase gene.

Although the above-mentioned closing and mutagenic oligonucleotides represent the embodiments used in this example, those skilled in the art will readily appreciate that the present invention is not limited to the use of these oligonucleotides sequences and comlementary sequences thereof. The following closing oligonucleotides and complementary sequences thereof also fall within the scope of the present invention:

(AatII)    5'TGGTTTCTTAGACGTCAGGTGGCACTTTTC;
(AflIII)   5'CTGGCCTTTTGCTCACATGTTCTTTCCTGC;
(AseI)     5'CTTCCCGGCAACAATTAATAGACTGGATGG;
(MstI)     5'TGGCAACAACGTTGCGCAAACTATTAACTG;
(NdeI)     5'GTATTTCACACCGCATATGGTGCACTCTCA;
(PstI)     5'ACCACGATGCCTGCAGCAATGGCAACAACG;
(PvuI)     5'ACTTCTGACAACGATCGGAGGACCGAAGGA;
(ScaI)    5'ATGACTTGGTTGAGTACTCACCAGTCACAG;
(SspI)    5'AAATGCTTCAATAATATTGAAAAAGGAAGA;
(XmnI)    5'TCGCCCCGAAGAACGTTTTCCAATGATGAG;

However, it is to be understood that these typical examples of closing oligonucleotides are introduced to illustrate rather than limit the scope of the present invention. In fact, any oligonucleotide having the ability to hybridize to at least the free ends of either a linear DNA strand or a circular DNA strand previously digested at a common restriction site can be used in the context of the present invention.

Standard Complementary-Strand
Synthesis-Site-Directed Mutagenesis Protocol

Unless indicated otherwise, reactions were performed as follows. 0.1 pmole of template DNA was mixed with 2 pmoles of closing oligonucleotide and 10 pmoles of mutagenic oligonucleotide and the final volume adjusted to 22 μl with water. To this mixture, 3 μl of annealing buffer (200 mM Tris-HCl, pH 7.4, 20 mM MgCl₂, and 500 mM NaCl) was added and the mixture was incubated in a boiling water bath for 3 minutes then transferred to ice. After incubation on ice for 2 to 8 minutes, 3 μl of DNA synthesis buffer (300 mM Tris-HCl, pH 7.8, 80 mM MgCl₂, 100 mM DTT, 10 mM ATP, 5 mM each of dGTP, dATP, dTTP and dCTP, and 500 μg/ml BSA), 1 μl of T4 DNA ligase (1 u/μ), and 1 μl of Klenow polymerase (7 u/μl) were added and incubation on ice continued for an additional 30 minute period. The reaction mixture was then transferred sequentially to room temperature for 30 minutes and 37° C. for 60 minutes. At this point, the reaction mixture was either stored at 4° C. or one half of their final volume used directly to transform 200 μl of competent HB2151 *E. coli* cells. Preparation of competent cells and transformation reactions were performed according to the method of Hanahan referred to above. The density of the various competent cells batches was pre-adjusted such that 200 μl of competent cells gave an efficiency of about $1 \times 10^6$ transformants per μg of pUC19 DNA. One tenth of the final transformation volume (100 μl) was spread onto rich plates containing 100 μg/ml ampicillin, 30 μM IPTG and 30 μg/ml X-Gal. The number of blue and white colonies was counted and the relative proportion of mutants expressed as a percentage of the total.

A schematic representation of the sequence of steps and expected structures for the standard site-directed mutagenesis reaction is shown in FIG. 1 where the target gene for mutagenesis is indicated by a heavy line. Uracil-substituted DNA strands are represented by a line with an occasional "u". The oligonucleotides are also shown as a heavy line with an arrowhead at the 3' end. The mutagenic oligonucleotide contains an inflection denoting the mismatch. In brackets, the expected structure for the "flush" closing oligonucleotide is depicted; that for the more effective "overlapping" closing oligonucleotide is shown in the main body of the figure (structure IV).

Characterization of the Complementary-Strand
Synthesis and Site-Directed Mutagenesis Process of the
Present Invention Characterization of the process of the present invention was initially performed by evaluating the transformation efficiency of the standard uracil-substituted, linear templates (FIG. 1, structure III) with or without treatment with various complementary-strand synthesis components.

Reactions were carried out as described above including all buffers and manipulations but containing only the indicated DNA synthesis components. The concentrations per reaction were 0.1 pmole of standard template (linearized, uracil-substituted pUC19 or pSNS282 DNA), 2 pmole of oligonucleotide, and 7 units of the Klenow enzyme and 1 unit of T4 DNA ligase, as required.

Results are summarized in Table 1 below, where the values given are an average of 7 experiments.

TABLE 1

| Complementary-strand formation as indicated by DNA synthesis-dependent increase in the transformation efficiency of linearized uracil-substituted DNA | |
|---|---|
| Reaction components | Colonies per plate |
| Template | 3 |
| Template + overlapping closing oligo | 5 |
| Template + flush closing oligo | 0 |
| Template + polymerase and ligase | 4 |
| Template + overlapping closing oligo + polymerase and ligase | 88 |
| Template + flush closing oligo + polymerase and ligase | 23 |

It can be seen from this table that only conditions which support DNA synthesis result in enhanced efficiency of transformation. In the absence of DNA synthesis, the number of transformants observed is close to zero, indicating that the template itself, even in combination with other components of the reaction, contributes minimally to the background.

Table 1 also shows that the overlapping closing oligonucleotide is nearly 4-fold more effective than the flush closing oligonucleotide (FIG. 1, structure IV) in producing transformation competent molecules. The reason for this may be related to enhanced ligation efficiency and better protection of the free ends of the template strand by the overlapping structure. Because of its greater effectiveness, the overlapping closing oligonucleotide was selected for use in all subsequent experiments.

Further evidence for full-length complementary-strand synthesis and the evaluation of the present strategy for application to site-directed mutagenesis were obtained by performing complete reactions (FIG. 1) using the B2W and W2B test systems. The experiments were performed as described above using 0.1 pmole template, 2 pmole overlapping closing oligonucleotide and 10 pmole mutagenic oligonucleotide. Results are shown in Table 2 where the values given are an average of 16 and 9 independent experiments for the B2W and W2B systems, respectively.

TABLE 2

Site-directed mutagenesis of the two test systems, B2W and W2B, by complementary-strand synthesis using double-stranded DNA templates.

| System | Colonies per plate | % Mutants |
|---|---|---|
| B2W | 62 | 49 |
| W2B | 57 | 31 |

The data in Table 2 show that inclusion of a mutagenic oligonucleotide appropriately alters the phenotype of the newly synthesized strand at high frequencies. The lower mutant formation efficiency observed for the 2-base insertion mutagenesis in the W2B system is presumably a consequence of a weaker mutagenic oligonucleotide-template duplex since such lower efficiency could be improved by elevation of oligonucleotide concentration as shown in FIG. 2, where Panel A shows the number of colonies obtained as a function of increasing concentrations of the overlapping closing oligonucleotide. Standard reactions were carried out as described above using 0.1 pmoles of linearized pUC19 or pSNS282 uracil-substituted DNA templates and no mutagenic oligonucleotides. Panel B shows the effects of increasing concentrations of the B2W (triangles) or W2B (circles) mutagenic oligonucleotides on the efficiency of site-directed mutagenesis. Reactions using components of the B2W or W2B system were performed as described above using 0.1 pmoles of template DNA and 2 pmoles of overlapping closing oligonucleotide.

In order to verify the presence of the intended alterations, plasmid DNA from mutant colonies selected at random and from different site-directed mutagenesis reactions using the B2W and W2B systems, were cleaved by the restriction enzymes DraI and XhoI, respectively. All mutant colonies tested yielded plasmid DNA containing the appropriate concomitantly created restriction enzyme site. Moreover, no plasmid rearrangement or multiple introduction of the restriction sites had taken place as indicated by these and other restriction enzyme analyses.

Characteristics and Requirements of the Site-Directed Mutagenesis Reaction

Table 3 shows the results of experiments in which the dependence of site-directed mutagenesis on the individual components or treatment steps of the standard reaction protocol was explored.

Reactions were carried out as described above except that the indicated component or step was omitted. The values given are an average of 3 independent experiments.

TABLE 3

Characteristics and requirements of the site-directed mutagenesis reaction.

| Component/Step | B2W system Colonies | B2W system % Mutants | W2B system Colonies | W2B system % Mutants |
|---|---|---|---|---|
| Complete reaction | 64 | 46 | 47 | 30 |
| No template | 0 | — | 0 | — |
| No closing oligo | 5 | — | 4 | — |
| No mutagenic oligo | 51 | — | 47 | — |
| No annealing buffer | 0 | — | 0 | — |
| No polymerase | 4 | — | 17 | — |
| No ligase | 0 | — | 2 | — |
| No denaturation step | 7 | — | 1 | — |
| No ice incubation step[a] | 44 | 56 | 53 | 37 |
| No RT incubation step[b] | 30 | 40 | 14 | 15 |
| No 37° C. incubation step[c] | 53 | 53 | 40 | 35 |

[a]Following the denaturation step, the reaction was placed at room temperature; and after the addition of dNTP, polymerase and ligase, it was kept at room temperature for 60 min. then transferred to 37° C. for 60 min.
[b]At the end of the 30 min. incubation period on ice, this reaction was transferred directly to 37° C.
[c]For this reaction, the last 60 min. at 37° C. was replaced by 60 min. at room temperature.

It is evident that omission of any one of the reaction components or the template denaturation step results in complete loss of mutant formation activity. On the other hand, elimination of the ice and/or 37° C. incubation steps appears to slightly improve the frequency of mutant molecules.

The activity of several DNA polymerases other than the Klenow enzyme has also been evaluated under standard conditions. As judged by the number of transformants and the relative proportion of mutant colonies obtained, E. coli polymerase I functioned about as well as the Klenow fragment, while T4 and T7 polymerase were less effective. M-MLV reverse transcriptase and Taq polymerase gave little or no activity under the experimental conditions set forth above. However, it is to be understood by those skilled in the art that variations of one or more of the experimental parameters could lead to substantial increases in those instances where enzymatic activity is weak or non-existant.

The potential of covalently-closed circular DNA for use as substrates under the present site-directed mutagenesis conditions has also been examined. In order to do so, uracil-containing supercoiled DNA was substituted for the linear template DNA and subjected to site-directed mutagenesis (B2W system without a closing oligonucleotide) using the standard reaction conditions or the standard conditions in which alkaline instead of heat denaturation was performed. The results of several independent experiments revealed that only 5 to 10% of the transformants have the mutant phenotype. The reason for this reduced frequency of mutagenesis is due to a substantial increase in the level of the background and perhaps to a larger extent on inefficient and/or incomplete complementary-strand synthesis. It may be possible to improve the efficiency of mutagenesis using uracil-substituted supercoiled templates and the present conditions for complementary-strand synthesis by treatment of the heteroduplex with uracil glycosylase and alkali to reduce the background as shown in Proc. Natl. Acad. Sci., USA 82, 488–492 (9185) or by introducing a single-stranded nick in the DNA as described in Science 209, 1396–1400 (9180), in order to generate usable circular templates.

The process of the present invention has been successfully applied to plasmid systems other than the B2W and W2B test systems and appears to be of general applicability as shown in Table 4.

TABLE 4

| Plasmid | Size, kilobases | Mutations introduced. | | Length of oligo | Screening method | Efficiency of mutagenesis |
|---|---|---|---|---|---|---|
| | | Gene mutated | Mutation introduced | | | |
| pUC19 | 2.8 | lacZα | TAC--AAA | 33 | color/RE | 50 (see text) |
| pSNS282 | 2.8 | lacZα | TA--TCGA | 32 | color/RE | 30 (see text) |
| pJWL184 | 4.0 | LexA | AT--CC | 32 | RE | 44 (4/9) |
| pJWL184 | 4.0 | LexA | AG--CC | 32 | RE | 33 (4/12) |
| pGEM-TAC-ONCO | 3.5 | Oncomodulin | A--T | 22 | Sequencing | 66 (4/6) |
| pGEM-TAC-ONCO | 3.5 | Oncomodulin | AA--TG | 21 | Sequencing | 60 (3/5) |

The mutagenesis reactions were performed as described above using the overlapping closing oligonucleotide.
The plasmids pUC19, pJWL184 and pGEN-TAC-ONO respectively described in Yanisch-Perron, C., Vieira, J., and Messing, J. (1985) Gene 33, 103–119, Lin, L-L., and Little, J. W. (1988) J. Bacteriol. 170, 2163–2173 and MacManus, J. P., Hutnic, C. M. L., Sykes, B. D., Szabo, A. G., Williams, T. C., and Banville, D. (1989) J. Biol. Chem. 264, 3470–3477, have been constructed in other works; pSNS282 was constructed as described above.
RE indicates that screening was performed by checking for a newly created restriction enzyme site.
The values given are the percentage of mutants followed in parentheses by the number of mutants obtained out of the total screened.

We claim:

1. A process for conducting site-directed mutagenesis on double-stranded DNA previously cleaved and denatured to single-stranded linear DNA templates, said process comprising
   (a) hybridizing mutagenic and closing oligonucleotides to single-stranded linear DNA templates, said closing oligonucleotide being characterized by having a nucleotide sequence complementary to one or both of the free ends of said linear DNA templates, and functioning to circularize said linear DNA templates and generate a primer-circular template structure suitable for polymerase-dependent full-length complementary-strand synthesis and ligation into a covalently-closed heteroduplex DNA molecule,
   (b) incorporating said mutagenic and closing oligonucleotides into DNA strands complementary to said linear DNA templates by submitting said hybridized linear DNA templates to the action of polymerase and ligase enzymes to yield heteroduplex double-stranded DNA molecules, and
   (c) selectively replicating said complementary DNA strands of said heteroduplex double-stranded DNA.

2. A process according to claim 1, which further comprises an initial step through which said double-stranded DNA is cleaved and denatured to yield single-stranded linear DNA templates.

3. A process according to claim 1, wherein said double-stranded DNA is a plasmid or any autonomous replicon.

4. A process according to claim 1, wherein said closing oligonucleotide has a nucleotide sequence complementary to the free ends of said linear DNA templates to anneal to both free ends of said linear DNA templates upon hybridization to cause circularization of said linear DNA templates.

5. A process according to claim 1, wherein said closing oligonucleotide has a sequence complementary to the 3' end of said linear DNA templates thereby creating blunt-ended molecules upon hybridization to said linear DNA templates.

6. A process according to claim 1, wherein said complementary DNA strands are selectively replicated by initially propagating said double-stranded DNA in a dut⁻ ung⁻ bacterial strain to obtain uracil-substituted DNA templates and then transforming said heteroduplex DNA molecules into a dut⁺ ung⁺ bacterial strain to obtain the desired mutant molecules.

7. A process according to claim 1, wherein said closing oligonucleotides are selected from the group consisting of the following:

(AatII)    5'TGGTTTCTTAGACGTCAGGTGCACTTTTC;
(AflIII)   5'CTGGCCTTTTGCTCACATGTTCTTTCCTGC;
(AseI)     5'CTTCCCGGCAACAATTAATAGACTGGATGG;
(MstI)     5'TGGCAACAACGTTGCGCAAACTATTAACTG;
(NdeI)     5'GTATTTCACACCGCATATGGTGCACTCTCA;
(PstI)     5'ACCACGATGCCTGCAGCAATGGCAACAACG;
(PvuI)     5'ACTTCTGACAACGATCGGAGGACCGAAGGA;
(ScaI)     5'ATGACTTGGTTGAGTACTCACCAGTCACAG;
(SspI)     5'AAATGCTTCAATAATATTGAAAAAGGAAGA;
(XmnI)     5'TCGCCCCGAAGAACGTTTTCCAATGATGAG; 5'CTGTGACTGGTGAGTACTCAACCAAGTCAT;

and complementary sequences thereof.

8. A kit for conducting site-directed mutagenesis of double-stranded DNA previously cleaved and denatured to single-stranded linear DNA templates, said templates being hybridized to mutagenic and closing oligonucleotides incorporated into DNA strands complementary to said templates, said kit comprising:
   (a) one or more closing oligonucleotides having a nucleotide sequence complementary to one or both of the free ends of said linear DNA templates, said oligonucleotide being characterized and functioning to circularize said linear DNA templates and generate a primer-circular template structure suitable for polymerase-dependent full-length complementary-strand synthesis and ligation into a covalently-closed heteroduplex DNA molecule, and
   (b) means for selective replication of said complementary DNA strands.

9. A kit according to claim 8, wherein said closing oligonucleotides are selected from the group consisting of the following:

(AatII) 5'TGGTTTCTTAGACGTCAGGTGGCACTTTTC;
(AflIII) 5'CTGGCCTTTTGCTCACATGTTCTTTCCTGC;
(AseI) 5'CTTCCCGGCAACAATTAATAGACTGGATGG;
(MstI) 5'TGGCAACAACGTTGCGCAAACTATTAACTG;
(NdeI) 5'GTATTTCACACCGCATATGGTGCACTCTCA;
(PstI) 5'ACCACGATGCCTGCAGCAATGGCAACAACG;
(PvuI) 5'ACTTCTGACAACGATCGGAGGACCGAAGGA;
(ScaI) 5'ATGACTTGGTTGAGTACTCACCAGTCACAG;
(SspI) 5'AAATGCTTCAATAATATTGAAAAAGGAAGA;
(XmnI) 5'TCGCCCCGAAGAACGTTTTCCAATGATGAG; 5'CTGTGACTGGTGAGTACTCAACCAAGTCAT;

and complementary sequences thereof.

10. A kit according to claim 8, wherein said closing oligonucleotides have a nucleotide sequence complementary to the free ends of said linear DNA templates to anneal to both free ends of said linear DNA templates upon hybridization to cause circularization of said linear DNA templates.

11. A kit according to claim 8, wherein said means for selective replication of the mutant plasmid is selected from propagation of said double-stranded DNA in a dut⁻ ung⁻ bacterial strain, incorporation of thionucleotides into said complementary DNA strands, or differential methylation.

* * * * *